United States Patent [19]

Johnston et al.

[11] Patent Number: 5,055,188

[45] Date of Patent: Oct. 8, 1991

[54] MAGNETIC APPARATUS FOR CONTROLLING PROTISTA IN DISTILLATES

[75] Inventors: John A. Johnston, Lower Hutt; Lindsay W. Forrest, Upper Hutt; Colin P. Wickham, Auckland, all of New Zealand

[73] Assignee: Debug Filters Limited, Lower Hutt, New Zealand

[21] Appl. No.: 430,960

[22] Filed: Nov. 1, 1989

Related U.S. Application Data

[63] Continuation of Ser. No. 122,873, Nov. 19, 1987, abandoned.

[30] Foreign Application Priority Data

Nov. 19, 1986 [NZ] New Zealand .................. 218331

[51] Int. Cl.$^5$ .................. B01D 35/06; C02F 1/48
[52] U.S. Cl. .................. 210/222; 123/538; 210/695
[58] Field of Search .................. 210/222, 223, 695; 202/254, 270, DIG. 1; 196/133, 136, 137, 155; 123/538

[56] References Cited

U.S. PATENT DOCUMENTS

| 2,652,925 | 9/1953 | Vermeiren | 210/222 |
| 4,519,919 | 5/1985 | Whyte et al. | 210/222 |
| 4,716,024 | 12/1987 | Pera | 210/222 |

FOREIGN PATENT DOCUMENTS

| 62-180792 | 8/1987 | Japan | 210/222 |
| WO84/04294 | 11/1984 | PCT Int'l Appl. | 210/222 |
| 148904 | 2/1955 | Sweden | 210/222 |
| 1313811 | 5/1987 | U.S.S.R. | 210/222 |

Primary Examiner—Joye L. Woodard
Attorney, Agent, or Firm—Fleit, Jacobson, Cohn, Price, Holman & Stern

[57] ABSTRACT

Apparatus for the control of Protistal growth in distillates including a flow path through which the hydrocarbon distillate is caused to flow, and a magnet assembly for producing a magnetic field in or about the flow path so that distillate flowing through the flow path is passed circuitously through the magnetic field.

6 Claims, 3 Drawing Sheets

MAGNETIC APPARATUS FOR CONTROLLING PROTISTA IN DISTILLATES

This is a continuation of application Ser. No. 07/122,873, filed Nov. 19, 1987, now abandoned.

BACKGROUND OF THE INVENTION

This invention relates to a method and an apparatus for the control of biological growth and by-products thereof in hydrocarbon distillates. More particularly, to control of microbiological growth and organic acids in liquid-fuel systems, particularly systems where the fuel is gasoline, including aviation gasoline, or diesel fuels.

There are species of Protista which grow, and under certain circumstances even flourish within fuels and lubricants derived from the hydrocarbon distillation process. These use the above-mentioned fuels and lubricants as their source of nutrition.

"Protista" as used herein includes all lower organisms, such as algae, bacteria, fungi, and protozoans. The growth of such Protista within feed lines of such fuel systems, or in storage portions of such fuel systems causes impairment of the system. Typical features are blocked feed lines and clogged fuel filters, and accelerated wear of, for example, injection equipment due to secreted organic acids.

The use of liquid-fuelled internal combustion engines is widespread. For example, much transport of goods and commerce relies on such engines for basic transport, but also in relation to such machines as hydraulic hoists, pumps, lifts and the like, and also in motors in heating and cooling systems. While the major problems of Protistal growth currenty relate principally to engines using automotive gas, oil (diesel) and kerosene (jet fuel), this invention is equally applicable to any unit using fuels/lubricants derived from the crude oil distillation process.

A typical example of problems involving cooling systems is provided by refrigerated containers. These are commonly supplied with a small cooling system utilizing a small internal combustion engine. The quality of the products transported in such containers, particularly food products, is dependent on the ability of the system to maintain a pre-selected temperature. The infestation of the fuel system with Protista decreases the efficiency of the system, occasionally to such a point that complete breakdown occurs.

Investigation into efficacious chemical additives for fuel systems to chemically control or eliminate the growth of these Protista continues, but the additives themselves may adversely affect the performance of the fuel, and do not deal with the accumulation of dead growth. In addition, it is a process entailing some considerable expense, and may require careful monitoring, or surveillance of chemical levels within the fuel itself. It is accordingly an object of this invention to provide an apparatus and a method for controlling Protistal growth and by-products thereof in hydrocarbon distillates, particularly in liquid fuels and lubricants.

It is a further object to provide an apparatus and a method for controlling Protistal growth which is simple to install, easy to maintain, and which has substantially no other effects upon the fuel or the fuel systems.

The use of magnetic fields for treatment of fluids is known, principally in relation to the removal of scale forming or corrosive materials from fluids. For example, New Zealand patents 172611, 94971, and 146614 deal with this aspect of magnetic treatment. In addition, the use of magnetic fields has been known in the treatment of fluids for removing ferromagnetic particles from fluids; New Zealand patent 156200 deals with this aspect of the use of magnetic fields.

The use of magnetic fields for inhibiting algae and bacteria in open, uncovered storage water is disclosed in New Zealand patent 182685.

However, there is in the prior art, no suggestion that the use of magnetic fields is efficacious in the control of Protista in distillates. The applicant has determined that magnetic fields are particularly effective, when applied to Protista in distillates, in inhibiting growth of such Protista. Further, the applicant has discovered that the magnetic fields may be applied to the fuel either between pumping from storage to holding tanks, or between holding tanks and the combustion engine or in bulk storage.

SUMMARY OF THE INVENTION

Accordingly, there is provided according to this invention apparatus for the control of Protistal growth in distillates comprising a length of line through which the hydrocarbon distillate containing Protista is caused to flow, and means for producing a magnetic field in or about the line.

According to a further aspect of the invention, controlling Protistal growth in distillates includes subjecting a flow of distillate containing Protista to a magnetic field produced by a magnetic producing means.

The applicant has conducted a number of trials aboard commercial cargo ships and fishing vessels, where the problem is known to exist, and has discovered that, by passing the fuel of these vessels through the apparatus according to this invention, the rate of Protistal growth in the fuels of such vehicles is dramatically reduced.

The applicant has discovered that the length of exposure of the Protista to the magnetic field, its strength and the rate of flow of the distillates containing Protista through the field are all factors relevant to the efficiency of the invention. The applicant has discovered that of prime importance is the entry and re-entry of the distillate into the, or several, magnetic fields. In order to achieve this, a series of magnets are used in connection with the fluid flow, configured to achieve a multi-pass system which is characterized in that the liquid flows in and around an array of magnets and baffles, thereby increasing the duration of the fluid flow contact with the magnetic field. Thus, by an apparatus of relatively simple construction, the efficiency of the magnetic field is enhanced.

The applicant has discovered that efficiency improves with increased time in the magnetic field. Desirably therefore the apparatus is constructed to permit high volumes of flow, at a slow rate.

BRIEF DESCRIPTION OF THE DRAWING

Various embodiments of apparatus according to the invention are possible; several are now given by way of non-limiting examples with reference to the accompanying drawings, wherein.

DESCRIPTION OF THE PREFERRED EMBODIMENTS

Figure 1:
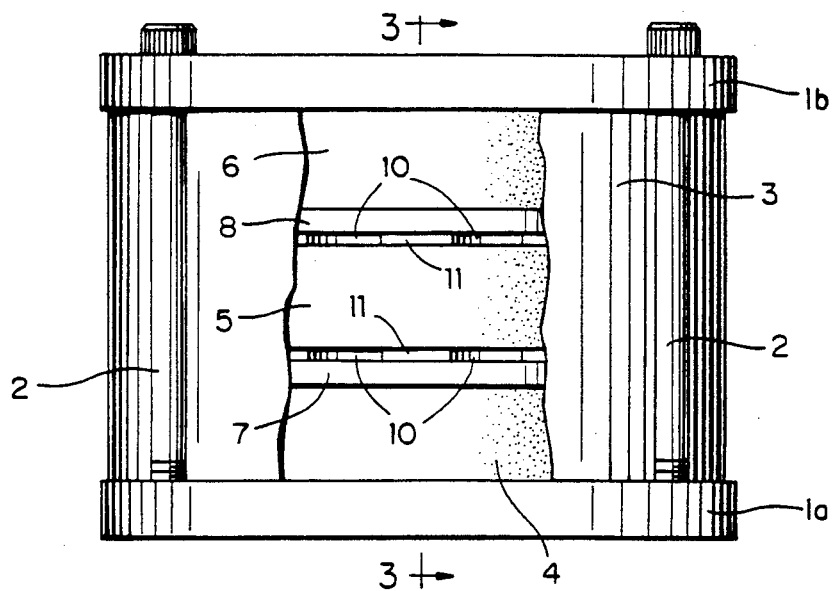
FIG. 1 is a side elevational view of a partially cut away embodiment of the apparatus of the invention.

FIG. 1 discloses a pair of mounting plates 1a and 1b, locked together by threaded restraining means 2. Side walls 3 are partially cut away to reveal within three substantially disc shaped magnets stacked vertically, 4, 5, and 6. The magnets are spaced apart from each other by spacers 7 and 8. Such an arrangement is referred to herein as a "stack". Magnets 4, 5 and 6 may be permanent magnets or electro-magnets of a type well known to persons having ordinary skill in the art. Therefore, further details of the magnets are not shown or described.

Figure 2:
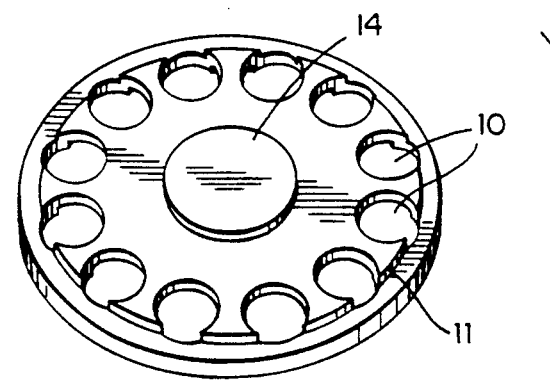
FIG. 2 is a perspective exploded view of a base plate and a spacing or stacking member of the apparatus of FIG. 1.
Figure 2:
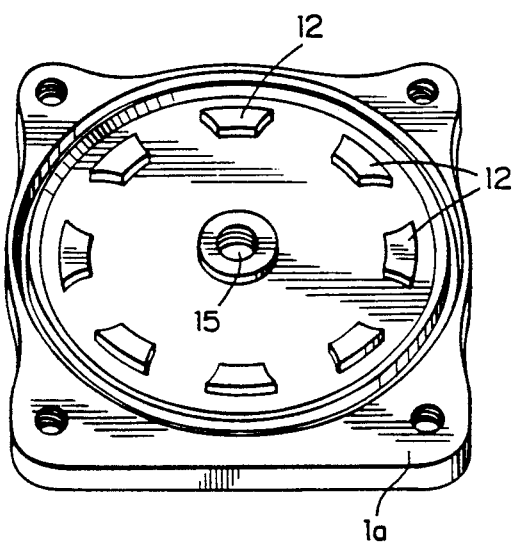

A perspective drawing of one of these spacers is shown in FIG. 2. It has a central solid raised disc portion 9 (see FIG. 3), and a series of spaced apart holes 10, close to the perimeter, and passing through a stepped, or shoulder portion 11.

Turning to the base member 1a shown in FIG. 2, it should be noted that there are a series of lands or spacers 12, upon which the lower magnet 4 sets.

Figure 3:
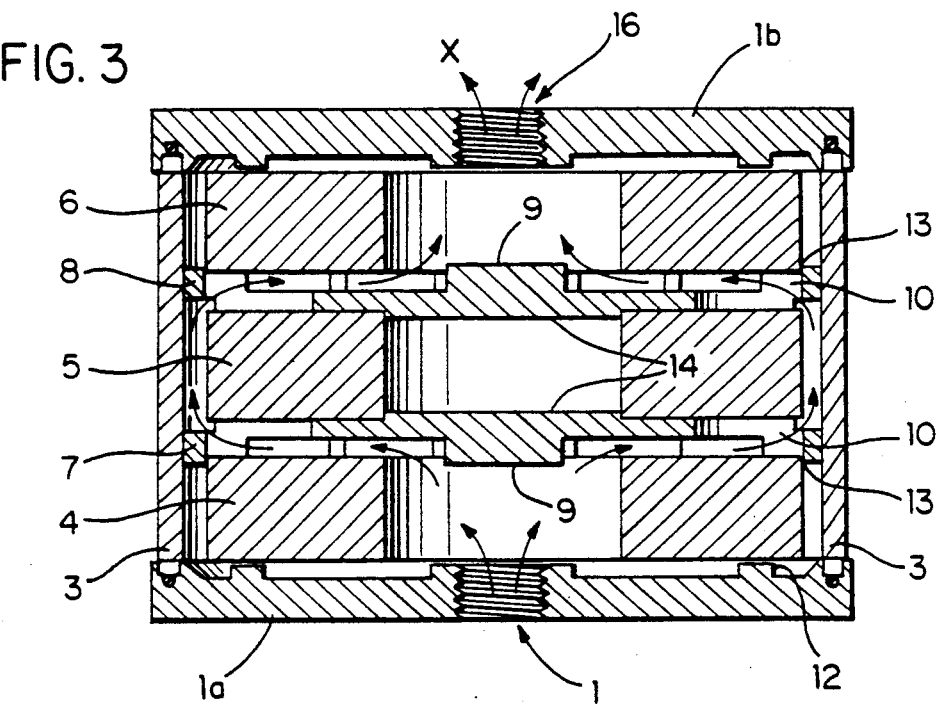
FIG. 3 is a vertical cross-sectional view through the center of the apparatus of FIG. 1.

FIG. 3 shows a section through the assemblage. It should be noted that the magnets 4,5, and 6 have a central hollow portion, which is co-axial with the center of the spacing members 7 and 8.

The spacing members are substantially the same diameter as the diameter of the chamber formed by the inner side of casing 3.

The outer periphery of each spacer contains a second stepped portion 13, which abuts and restrains magnets 6 and 4.

The spacers have a second raised disc portion 14, obverse from raised disk portion 9.

Raised portions 14 of spacers 7 and 8 are arranged facing each other, and dimensioned so as to fit tightly into the axial hole in magnet 5, thereby restraining it in position.

By virtue of the arrangements of the holes 10 in the spacers, the axial holes in the magnets 4, 5, and 6, and the spacing effect of spacers 7 and 8, a fuel flow may be passed through the apparatus, ingressing at aperture 15, through the axial hole of magnet 4, beneath spacer 7 and passing through holes 10 in spacer 7, around the cavity defined by the inner wall of container 3 and the outer wall of magnet 5, through holes 10 in spacer 8, then through the axial cavity of magnet 6, and egressing through aperture 16, as shown in FIG. 3 by direction arrows X.

In use it is envisaged that apertures 15 and 16 will be threaded, to permit engagement with a threaded fuel line.

It will be seen that the fuel flow is therefore through the centers of magnets 4 and 6, and around the outer perimeter of magnet 5.

Figure 4:
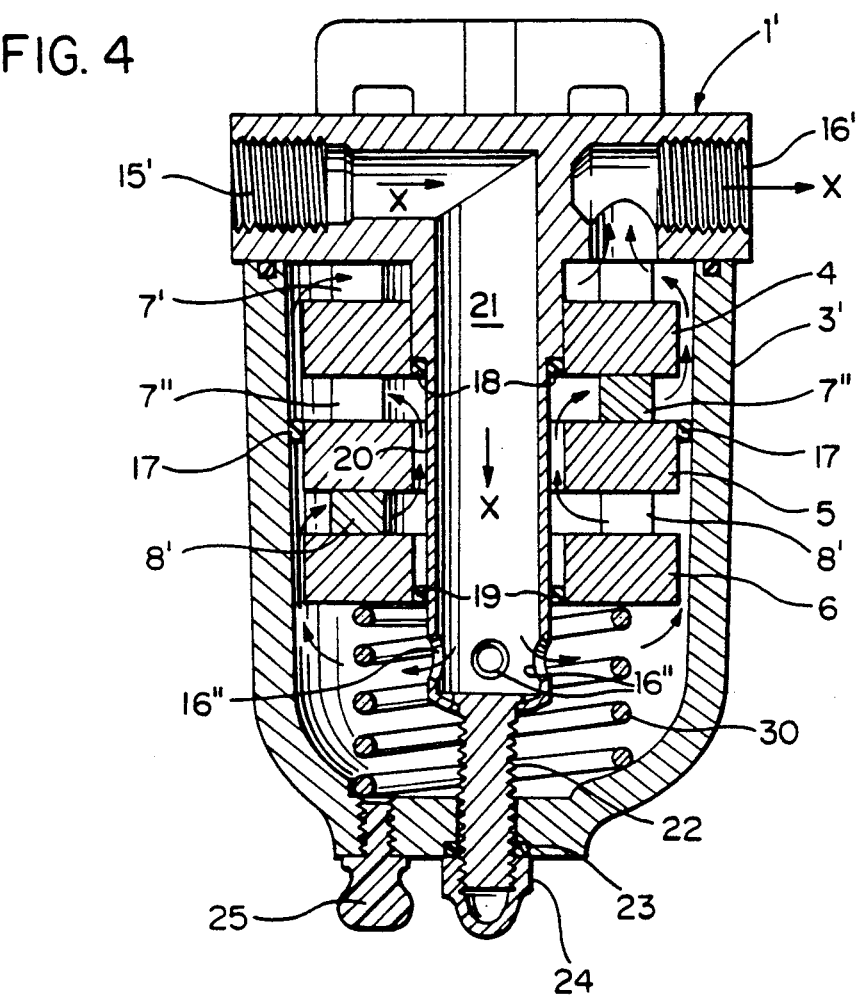
FIG. 4 is a view similar to FIG. 3 through a second embodiment.

FIG. 4 discloses a second embodiment, having a base plate 1', side walls 3' of a bowl shaped housing, stacked magnets 4, 5, and 6, separated by sets of spacers 1', 7" and 8'.

Each set of spacers is made up of three lugs around which the fuel may flow.

The magnets are arranged about an axial shaft 20 which has a threaded aperture 15' opening to a bore 21 which itself opens by means of a plurality of egress holes 16".

A coil spring 30 is provided which retains the stack of magnets in place on shaft 20. Shaft 20 terminates in a threaded portion 22, which passes through walls 3' to be retained by means of a sealing washer and cap nut, 23 and 24, respectively.

A stop cock 25 is also provided for draining the apparatus. It will be seen that fuel may flow in entry aperture 15', through bore 21, passing through the field created by each magnet, out through the holes 16", out across magnet 6, between the inside of wall 3' and magnet 6, across magnet 5, between magnet 5 and the shaft 20, across magnet 4, between the inside of wall 3' and magnet 4, and out through port 16'. This flow direction is reversable.

It will be appreciated that the flow thus winds in and out of the stack of magnets, moving in and out of the respective magnetic fields, and prolonging the duration of the period that the fluid is within a magnetic field.

Paired sealing means 17, by friction fit, retain magnet 5 in place: paired sealing means 18 and 19 similarly retain magnets 4 and 6, respectively, providing a fluid flow path X around the magnets. In the present embodiment, the sealing means are "O-rings".

Figure 5:
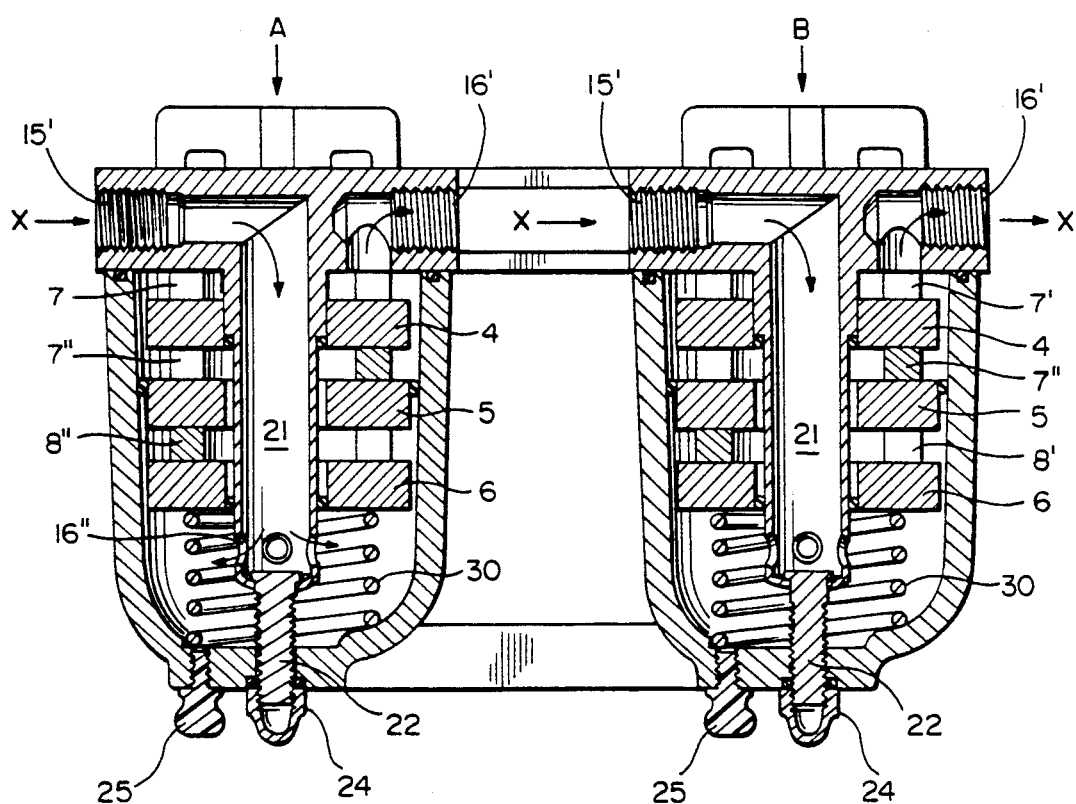
FIG. 5 shows a vertical section through an embodiment incorporating two units similar to those shown in FIG. 4 connected in series.

It will be appreciated that a multiplicity of units may be utilised. FIG. 5 shows one embodiment of such a multistage system, in which, briefly, two units of constructions similar to that depicted in FIG. 4 are shown connected that the flow egressing from a first unit A flows through the inlet of a second unit B, thus doubling the period of exposed field. The presently preferred embodiment, shown in FIG. 5, has two such units, but the applicant contemplates a multistage apparatus having three or more of such units, connected serially.

It will also be appreciated that a greater number of magnets may be so spaced within a suitably dimensioned container to increase the length of passage through the magnetic field.

The ends designed to be achieved mechanically, may be obtained by any suitable mechanical means which will be well known in the art.

It will be appreciated that the invention may be modified without parting from the scope of the invention.

Although reference here has been to a cylindrical system, with disc shaped magnets and spacers, it is envisaged that square or rectangular or other shapes may be usefully employed according to the invention.

Accordingly, there is provided by this invention a magnetic fuel treatment apparatus, and a method for magnetically treating fuel employing this apparatus.

What we claim is:

1. Apparatus for controlling Prodistal growth in distillates comprising:

a housing;

a hollow chamber defined in said housing;

inlet and outlet means in said housing for said chamber;

a plurality of magnets arranged in adjacent spaced relationship in said chamber between said inlet and outlet means for producing magnetic fields in said chamber;

apertures in said magnets for the flow of fluid therethrough; and spacer means between said magnets for spacing said magnets with respect to each other and with respect to said chamber, and for controlling the flow of fluid from said inlet to said outlet means so as to flow through the apertures in at least one of said magnets and flow around at least one other of said magnets adjacent to said at least one magnet so that said fluid flows circuitously through said chamber and cuts across the magnetic flux of said magnetic fields.

2. Apparatus as claimed in claim 1 wherein:

said magnets are substantially disc shaped and are spaced inwardly from the interior wall of said housing defining said chamber; and said apertures comprise a substantially central hole through each of said magnets.

3. Apparatus as claimed in claim 2 wherein:

said spacer means comprises a plurality of disc shaped spacers;

a plurality of flow directing holes in each of said spacers circumferentially spaced adjacent the periphery of each of said spacers;

a peripheral shoulder portion on each of said spacers for engaging an outer peripheral portion of an adjacent one of said magnets on one side of each of said spacers;

an inner shoulder portion on each of said spacers inwardly of said flow directing holes and engaging an adjacent one of said magnets on the other side of each of said spacers at said central hole of each of said magnets, so that said shoulder portions retain said magnets in substantially fixed position with respect to each other and with respect to said chamber; and flow channel means in each of said spacers on said one side of each of said spacers communicating said flow directing holes with said central hole of the adjacent magnet on said one side of each of said spacers.

4. Apparatus as claimed in claim 2 wherein:

said housing comprises a bowl shaped member having an open end;

a base plate is provided closing said open end;

said inlet and outlet means are in said base plate;

a tubular member extends through said central holes in said magnets and has one end communicating with said inlet means for guiding said flow through the centers of said magnets to said chamber adjacent the end of said plurality of magnets opposite to said inlet and outlet means; and at least one of said magnets is spaced at the central hole thereof from said tubular member so that fluid flow is directed circuitously around at least one of said magnets and through the center of at least another of said magnets to said outlet means.

5. Apparatus as claimed in claim 4 and further comprising:

spring means between said housing and said end of said plurality of magnets opposite to said inlet and outlet means for retaining said magnets in position within said chamber.

6. Apparatus as claimed in claim 4 and further comprising:

seal means between said magnets, housing, and tubular member for controlling the direction of fluid flow.

* * * * *